United States Patent [19]
Fearon et al.

[11] Patent Number: 5,998,604
[45] Date of Patent: Dec. 7, 1999

[54] POLYNUCLEOTIDE PURIFICATION METHOD

[75] Inventors: Karen L. Fearon, Lafayette; Victoria Lee Boyd, San Carlos, both of Calif.

[73] Assignees: The Perkin-Elmer Corporation, Foster; Lynx Therapeutics, Inc., Hayward, both of Calif.

[21] Appl. No.: 08/929,620

[22] Filed: Sep. 15, 1997

[51] Int. Cl.$^6$ .................................................. C07H 21/00
[52] U.S. Cl. .................... 536/25.4; 536/25.3; 536/25.34; 536/25.33; 536/23.1
[58] Field of Search ................................. 536/23.1, 25.4, 536/25.3, 25.33, 25.34

[56] References Cited

U.S. PATENT DOCUMENTS

| | | | |
|---|---|---|---|
| 5,281,701 | 1/1994 | Vinayak | 536/25.34 |
| 5,380,835 | 1/1995 | Celebuski et al. | 536/18.5 |
| 5,525,719 | 6/1996 | Srivastava et al. | 536/26.7 |
| 5,610,052 | 3/1997 | Thompson et al. | 435/366 |
| 5,622,854 | 4/1997 | Draper | 435/366 |
| 5,631,360 | 5/1997 | Usman et al. | 536/25.31 |
| 5,686,599 | 11/1997 | Tracz | 536/25.31 |

FOREIGN PATENT DOCUMENTS

| | | |
|---|---|---|
| WO 93/20091 | 10/1993 | WIPO . |
| 9728177 | 8/1997 | WIPO . |

OTHER PUBLICATIONS

Zon, "Purification of Synthetic Oligodeoxyribonucleotides," Ch. 14 in *High–Performance Liquid Chromatography in Biotechnology*, Hancock (ed.), John Wiley & Sons, New York, NY, 1990, pp. 301–397.

Kaplan et al., "DNA Synthesis on Solid Supports and Automation," Chapter 3 in *Synthesis and Applications of DNA and RNA*, Narang (ed.), Academic Press, Inc., New York, NY, 1987, pp. 9–45.

Reese, "Studies in the Synthesis of Oligo– and Poly–ribonucleotides," disclosed in *Synthetic Oligonucleotides: Problems ahd Frontiers of Practical Application, Nucleic Acids Symposium Series No. 24*, Moscow, USSR, Jun. 23–30, 1991, IRL Press, Oxford, UK, pp. 25–28.

Pfleiderer et al., "New Approaches Towards Automated Oligoribonucleotide Synthesis," disclosed in *Synthetic Oligonucletodies: Problems ahd Frontiers of Practice Application, Nucleic Acids Symposium Series No. 24*, Moscow, USSR, Jun. 23–30, 1991, IRL Press, Oxford, UK, pp. 29–32.

Celebuski, J.E. and Chan, C., "Synthesis and Utility of a DNA Phosphorylating Agent Based on 2–(Triphenylsilyl)ethanol," *J. Org. Chem.* 57: 5535–5538 (1992) (Issue No. 20).

Jenkins, L.A. et al., "The Embedded Ribonucleotide Assay: A Chimeric Substrate for Studying Cleavage of RNA by Transesterification," *J. Am. Chem. Soc.* 118: 6822–6825 (1996).(#29).

Jones, R.A. et al., "Use of the Lipophilic tert–Butyldiphenylsilyl Protecting Group in Synthesis and Rapid Separation of Polynucleotides," *Biochemistry*. 17: (07) 1268–1277 (1978).

Webster, K.R. et al., "A Rapid Method for Purification of Synthetic Oligoribonucleotides," *BioTechniques*. 11: (05) 658–661 (1991).

*Primary Examiner*—L. Eric Crane
*Attorney, Agent, or Firm*—LeeAnn Gorthey; Dehlinger & Associates

[57] ABSTRACT

A method of purifying a hydrophobically substituted polynucleotide by reverse phase HPLC is described. The hydrophobic substituent may be removed from the polynucleotide under non-acidic conditions; the purification method is thus especially useful for acid sensitive polynucleotide analogs.

20 Claims, 7 Drawing Sheets

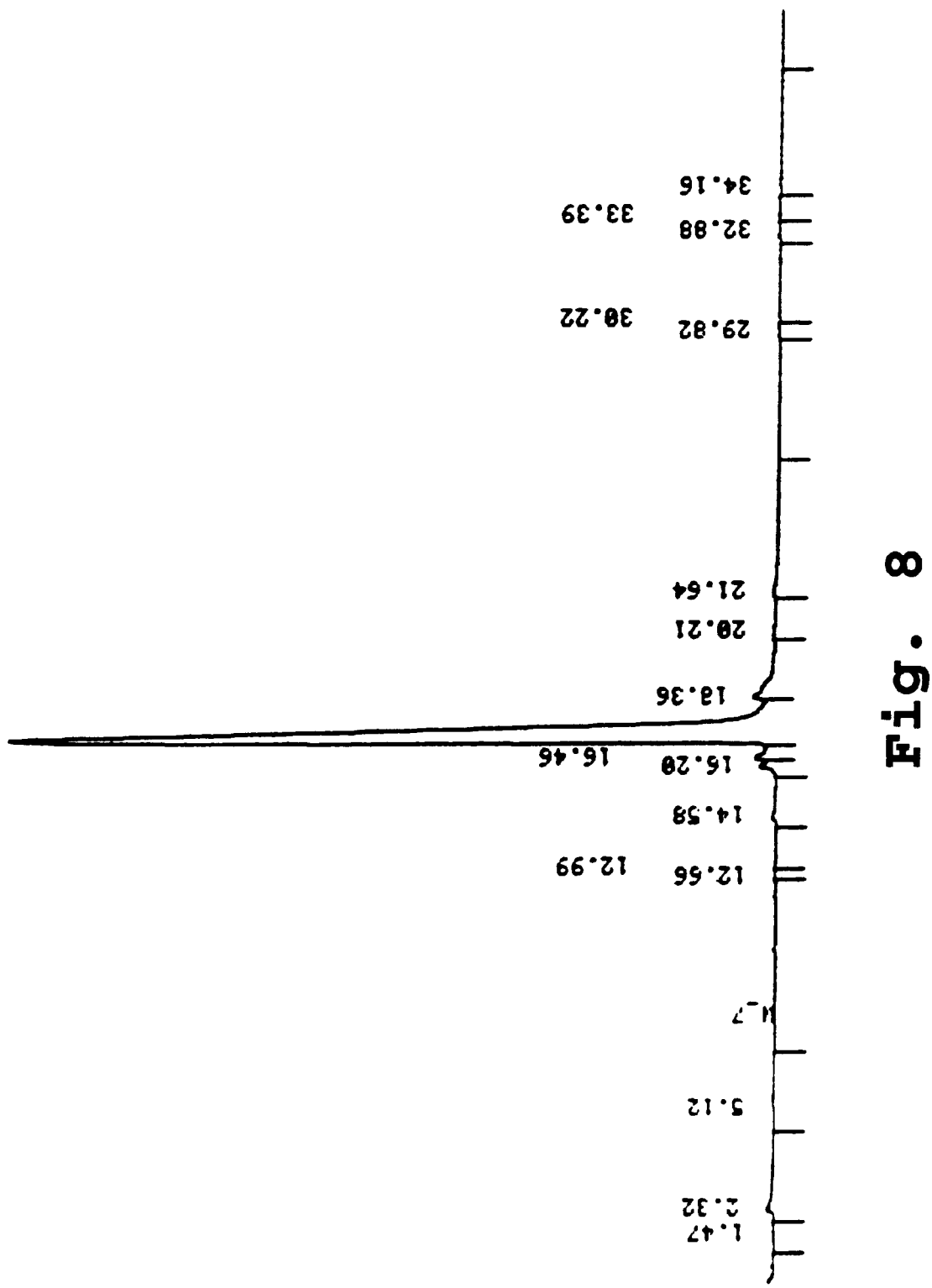

POLYNUCLEOTIDE PURIFICATION METHOD

FIELD OF THE INVENTION

The invention is directed to a hydrophobically substituted polynucleotide, and to a method of polynucleotide purification by reverse phase HPLC. The purification method is especially useful for acid sensitive polynucleotide analogs.

REFERENCES

Andrus et al., Tetrahedron Lett. 29:861–864 (1988).
Atkinson, T. et al., in *OLIGONUCLEOTIDE SYNTHESIS: A PRACTICAL APPROACH* (M. J. Gait, Ed.), IRL Press, Oxford (1984).
Beigelman, L. et al., *Bioorg. & Medicinal Chem. Lett.* (14):1715–20 (1994).
Caruthers et al., U.S. Pat. No. 4,458,066 (7/1984).
Caruthers et al., U.S. Pat. No. 4,500,707 (2/1985).
Froehler et al., *Nucleic Acids Res.* 14:5399–5407 (1986).
Froehler, *Tetrahedron Lett.* 27:5575–5578 (1986).
Froehler et al., *Tetrahedron Lett.* 27:469–472 (1986).
Garegg et al., *Tetrahedron Lett.* 27:4051–4054;4055–4058 (1986).
Germann et al., *Anal. Biochem.* 165:399–405 (1987).
Hakimelahi, G. et al., *Can. J. Chem.* 60(9):1106–13 (1982).
Ikuta et al., *Anal. Chem.* 56:2253–2256 (1984).
Jeong, L. S. et al., *J. Heterocyclic Chem.* 30:1445 (1993).
Jones, R. A., in *OLIGONUCLEOTIDE SYNTHESIS: A PRACTICAL APPROACH* (M. J. Gait, Ed.), IRL Press, Oxford (1984).
Kocienski, P. J., *PROTECTING GROUPS*, Georg Thieme Verlag, Stuttgart (1984).
Koester et al., U.S. Pat. No. 4,725,677 (2/1988).
Leeson, P. D. et al., *Bioorg. & Medicinal Chem. Lett.* 3(10):1925–30 (1993).
Markiewicz, W. T., *J. Chem. Res.* 1:24–25 (1979).
Matteucci et al., *J. Amer. Chem. Soc.* 103:3185–3191 (1981).
McCurdy, S. N. et al., *Tetrahedron Lett.* 38(2):207–210 (1997).
Molko et al., EP Patent Appn. No. 0241363 (1987).
Stec et al., *J. Am. Chem. Soc.* 106:6077–6079 (1984).
Usman et al., *J. Am. Chem. Soc.* 109:7845–7854 (1987).
Wallace et al., in *SOLID PHASE BIOCHEMISTRY* (Scouten, Ed.), John Wiley & Sons, New York, pp. 631–663 (1982).

BACKGROUND OF THE INVENTION

A key factor in the recent advances in molecular biology has been the development of reliable and convenient methods for synthesizing polynucleotides. As the use of synthetic polynucleotides has increased, the demand for greater convenience in the preparation of pure, ready-to-use polynucleotides has also increased. This demand has stimulated the development of many improvements in the basic procedures for solid phase synthesis and purification of polynucleotides. One such advance is the use of hydrophobic "handles", such as trityl moieties, in the rapid purification of synthetic oligonucleotides by reverse-phase HPLC (see, for example, Germann et al.; Ikuta et al.). This method presents advantages over ion exchange purification in that it is less time consuming and more readily scalable. The use of phosphorothioate linkages in polynucleotide analogs also reduces the resolution of ion exchange chromatography.

The RP-HPLC method can present difficulties in the purification of acid-sensitive polynucleotide analogs, however, because of the acidic conditions typically used for removal of the hydrophobic group. It would therefore be useful to have a hydrophobic purification handle that is stable to polynucleotide synthesis and ammoniolytic deprotection conditions, yet can be cleaved under mild, non-acidic conditions post purification.

SUMMARY OF THE INVENTION

The present invention includes, in one aspect, a method of purifying a polynucleotide product, which includes the following steps. First, there is formed a 3'- or 5'-polynucleotide cis-diol phosphate diester, as represented by formula I or II below:

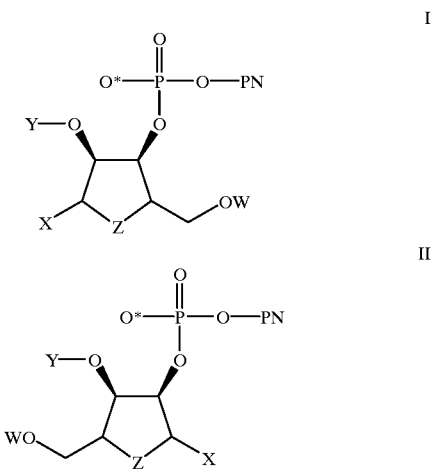

where PN comprises a polynucleotide chain, W is a hydrophobic group, X is selected from the group consisting of hydrogen, lower alkoxy, and nitrogen-linked heteroaryl, Y is hydrogen or a 2'- or 3'-hydroxyl protecting group, and Z is oxygen or —$CH_2$—. In separate preferred embodiments, the phosphate diester is represented by formula I, Z is oxygen, and X is a purine or pyrimidine base.

The phosphate diester I or II is selectively adsorbed onto a hydrophobic solid-phase support, and then eluted from the support to yield a purified polynucleotide product. In a preferred embodiment of the method, the 2'- or 3'-hydroxyl protecting group is then removed from the protected polynucleotide diol phosphate diester, and the resulting polynucleotide diol phosphate diester is treated with base, cleaving the diol phosphate moiety from the polynucleotide. In an alternative embodiment of this method, the protecting group Y is removed before the adsorbing step.

The polynucleotide product purified by this method may include one or more N3'→P5' phosphoramidate intersubunit linkages, one or more phosphodiester intersubunit linkages, one or more phosphorothioate intersubunit linkages, or one or more 2'-alkoxy RNA nucleotide subunits.

The hydrophobic group represented by W preferably includes an alkyl group having at least twelve carbon atoms, an aryl group containing at least two aromatic rings and at least 8 carbon atoms, or an aralkyl group comprising at least two aromatic rings and containing at least 9 carbon atoms. Preferably, the hydrophobic group is an unsubstituted or substituted trityl or pixyl group, and most preferably it is 4,4'-dimethoxytrityl.

The protecting group represented by Y is preferably a silane, $SiR^1R^2R^3$, where $R^1$, $R^2$ and $R^3$ taken separately are lower alkyl, lower haloalkyl, or aryl. Tert-butyl dimethyl silane, i.e. where $R^1=R^2$=methyl and $R^3$=tert-butyl, is especially preferred. Removal of the silane is preferably accomplished using fluoride ion.

The 3'- or 5'-polynucleotide cis-diol phosphate diester represented by formula I or II may be formed by reacting a polynucleotide having a free 3'- or 5'-hydroxyl group with a protected cis-diol phosphoramidite, as represented by formula A or B below. This reaction forms a phosphite triester, which is then oxidized to give a phosphate triester, and the protecting group Y is optionally removed.

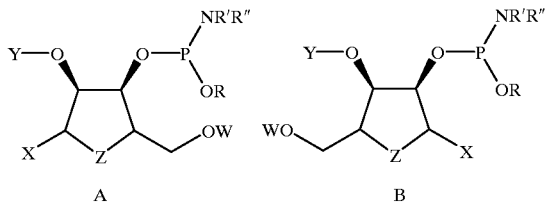

In formula A or B, W is a hydrophobic group, X is selected from the group consisting of hydrogen, lower alkoxy, and nitrogen-linked heteroaryl, Y is a 2'- or 3'-hydroxyl protecting group, Z is oxygen or —$CH_2$—, and R is a phosphate protecting group. R' and R" are separately alkyl, aryl, aralkyl, or $C_5$ to $C_{10}$ cycloalkyl, or R' and R" taken together with the nitrogen atom to which they are attached form a saturated 5- or 6-membered ring whose ring atoms are selected from carbon, nitrogen, oxygen, and sulfur. In separate preferred embodiments, the phosphoramidite is represented by formula A, and R' and R" are isopropyl.

In formula A or B, the phosphate protecting group represented by R is preferably methyl, lower alkyl beta-substituted with at least one electron-withdrawing group, or halo-substituted aryl. Most preferably, R is methyl or β-cyanoethyl.

The invention is also directed to a polynucleotide product, as represented by formula I or II, shown above, where PN comprises a polynucleotide chain, W is a hydrophobic group, X is hydrogen, lower alkoxy, or nitrogen-linked heteroaryl, Y is hydrogen or a 2'- or 3'-hydroxyl protecting group, and Z is oxygen or —$CH_2$—. In separate preferred embodiments, the polynucleotide product is represented by formula I, Z is oxygen, and X is a purine or pyrimidine base.

The protecting group Y is preferably a group cleavable under non-acidic conditions, such as a silane, $SiR^1R^2R^3$, where $R^1$, $R^2$ and $R^3$ taken separately are lower alkyl, lower haloalkyl, or aryl. Tert-butyl dimethyl silane, i.e. where $R^1$=$R^2$=methyl and $R^3$=tert-butyl, is especially preferred.

The hydrophobic group represented by W preferably includes an alkyl group having at least twelve carbon atoms, an aryl group containing at least two aromatic rings and at least 8 carbon atoms, or an aralkyl group comprising at least two aromatic rings and containing at least 9 carbon atoms. Preferably, the hydrophobic group is an unsubstituted or substituted trityl or pixyl group, and most preferably it is 4,4'-dimethoxytrityl.

These and other objects and features of the invention will become more fully apparent when the following detailed description of the invention is read in conjunction with the accompanying drawings.

BRIEF DESCRIPTION OF THE DRAWINGS

FIG. 8 shows an ion exchange chromatography (IEC) trace of the oligonucleotide of FIG. 7 after RP-HPLC purification, removal of the attached diol monophosphate ester with its hydrophobic substituent, and desalting.

DETAILED DESCRIPTION OF THE INVENTION

I. Definitions

Figure 1A:
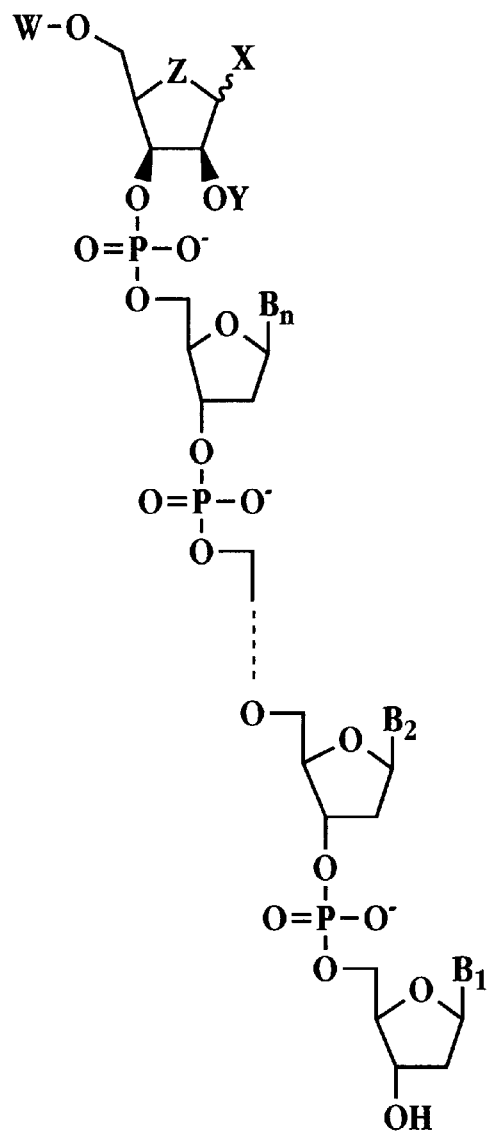
FIG. 1A shows a phosphate-linked polynucleotide product having a hydrophobically-substituted diol monophosphate ester group attached at the 5'-terminus, in accordance with one embodiment of the invention.

The terms below have the following meanings unless indicated otherwise.

As used herein, the term "polynucleotide" refers to a single stranded chain of either deoxyribonucleotides or 2'-alkoxy ribonucleotides, or a combination thereof, having from a few, e.g. 2–20, to many, e.g. 20 to several hundred or more, nucleotides. The term also includes chains of nucleosides linked by analogs of the phosphate bond, e.g. phorphoramidates, phosphorothioates, and the like, or combinations thereof.

The term "diol phosphate ester" or "diol monophosphate ester" refers to a diol of which one hydroxyl has reacted to form a phosphate ester, such as shown in structures I and II. The compound may also be referred to as a "diol phosphate triester or diol phosphate ester" when additional oxygens of the phosphate group are substituted, e.g. linked to a polynucleotide or an alkyl group. Similarly, a "protected diol phosphate ester" (or diester or triester) is such a compound in which the non-phosphate hydroxyl group is protected. Corresponding definitions apply to terms such as "protected diol phosphoramidite" (e.g. as represented by structures A and B).

A "derivatized polynucleotide" is a polynucleotide to which is attached a hydrophobically substituted diol phosphate ester, as defined above.

A "polynucleotide product" includes a derivatized polynucleotide as defined above, and a polynucleotide from which such a hydrophobically substituted diol phosphate ester has been removed after purification.

"Alkyl" refers to a fully saturated monovalent radical containing carbon and hydrogen, and which may be cyclic, branched or a straight chain. Examples of alkyl groups are methyl, ethyl, n-butyl, n-heptyl, isopropyl, 2-methylpropyl, cyclopropyl, cyclopropyl-methyl, cyclobutyl, cyclopentyl, cyclopentylethyl, and cyclohexyl. "Alkenyl" refers to such a group which is singly or multiply unsaturated.

"Lower alkyl" refers to an alkyl radical of one to six carbon atoms, as exemplified by methyl, ethyl, n-butyl, i-butyl, t-butyl, isoamyl, n-pentyl, and isopentyl. "Lower alkoxy" refers to alkoxy radicals derived from such groups.

"Aryl" refers to a substituted or unsubstituted monovalent aromatic radical having a single ring (e.g., benzene) or two or more condensed rings (e.g., naphthyl). Other examples include heterocyclic aromatic ring groups having one or more nitrogen, oxygen, or sulfur atoms in the ring, such as furyl, pyrrole, pyridyl, and indole. By "substituted" is meant that one or more ring hydrogens in the aryl group is replaced with lower alkyl, halogenated lower alkyl, nitro, amino, hydroxy, lower alkyl amino, lower alkoxy, or a halide such as fluorine, chlorine, or bromine.

"Alkaryl" refers to alkyl-substituted aryl, both as defined above, while "aralkyl" refers to aryl-substituted alkyl.

A "nitrogen-linked heteroaryl" substituent refers to a substituted or unsubstituted (as defined above) monovalent aromatic radical having a ring nitrogen through which it is connected to a parent structure. The heteroaryl group may have a single ring (e.g., pyrimidine, triazine, imidazole) or two condensed rings (e.g., purine, quinoline). Preferred nitrogen-linked heteroaryls are the DNA/RNA purine and pyrimidine bases, adenine, guanine, cytosine, thymine, and uracil.

"Trityl" refers to the triphenylmethyl radical and electron-donating-substituted derivatives. Preferred electron-donating substituents include amino, $C_1$–$C_6$ alkyl, $C_6$–$C_{12}$ aryl, $C_1$–$C_6$ alkoxy, and the like. Exemplary trityl groups include 4,4-dimethoxytrityl (DMT), monomethoxytrityl, α-naphthyldiphenylmethyl, tri(p-methoxyphenyl)methyl, 4-(4'-bromophenacyl oxyphenyl) diphenylmethyl, 4,4', 4"-tris (benzoyloxy-phenyl)methyl, and the like.

II. Polynucleotide Product with Attached Hydrophobic Diol Phosphate Ester

A. Polynucleotide Component

Figure 1B:
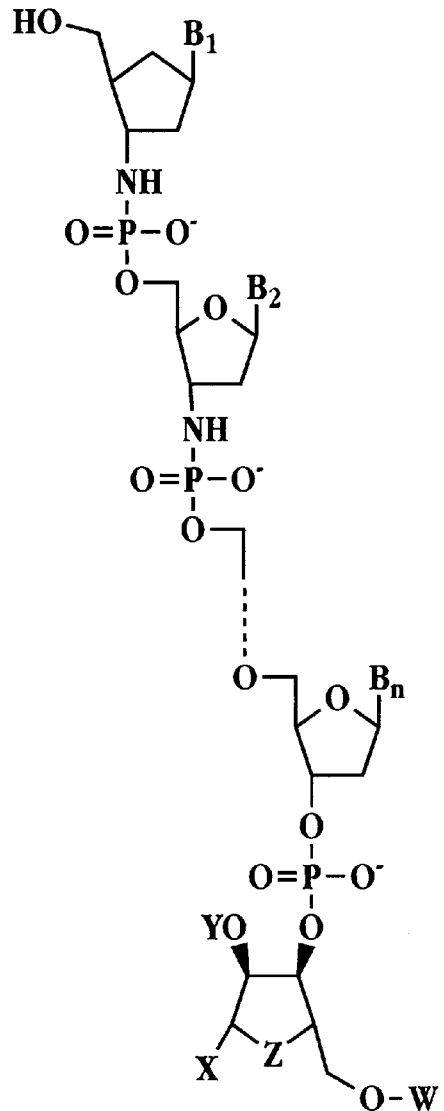
FIG. 1B shows a N3'→P5' phosphoramidite, a polynucleotide analog, with a similar group attached at the 3'-terminus.

The invention provides, in one aspect, a poly-nucleotide having attached thereto a hydrophobically substituted cyclic moiety, specifically a cyclic cis-diol phosphate ester substituted with a hydrophobic group, as represented by structures I and II above. Specific examples are shown in FIGS. 1A–1B, described further below.

The polynucleotide may be a "natural", phosphate-linked polynucleotide, or it may be any of a wide variety of known polynucleotide analogs. These include polynucleotides wherein the internucleotide linkages are, for example, phosphoramidate, phosphorothioate, or phosphodiester linkages, or a combination thereof, forming a chimeric polynucleotide analog. Also included are 2'-alkoxy RNA analogs and 2'-alkoxy RNA/DNA chimeras, where the polynucleotide includes at least one 2'-alkoxy RNA nucleotide subunit. Such analogs are resistant to nucleases, unlike natural polynucleotides, and are thus promising candidates for therapeutic and diagnostic applications.

B. Attached Hydrophobic Diol Phosphate Ester

Attached to the polynucleotide, preferably at its 5'-terminus if it has been prepared in a 3'to 5'direction, or at its 3'-terminus if it has been prepared in a 5'to 3'direction, is a cyclic diol phosphate ester with a hydrophobic substituent. FIG. 1A shows a "natural" phosphate-linked polynucleotide with the cyclic moiety attached at the 5'-terminus, and FIG. 1B shows a N3'→P5' phosphoramidite, a recently developed polynucleotide analog, with the cyclic moiety attached to its 3' terminus. In the Figures, $B_n$ represents a purine or pyrimidine base, W is a hydrophobic group, X is hydrogen, lower alkoxy, or a nitrogen-linked heteroaryl substituent, Y is hydrogen or a 2'- or 3'-hydroxyl protecting group, and Z is —$CH_2$— or oxygen.

The attached hydrophobic moiety comprises a diol phosphate ester in which the phosphate group, linked to the polynucleotide, is in a 1,2-cis relationship with the adjacent hydroxyl group, as shown. Although a specific absolute configuration of the cis-diol is depicted, it is understood that the cis-diol may also have the opposite absolute configuration to that shown, or be a mixture of absolute configurations. During preparation and/or purification of the polynucleotide, the free hydroxyl of the cyclic diol is protected, as described further below.

The cyclic moiety is further substituted with a hydrophobic group, as represented by W. This hydrophobic substituent is effective to allow the polynucleotide containing the cyclic moiety to be separated from other species, i.e. those not containing the hydrophobic substituent, by chromatographic methods such as reverse phase HPLC. (See, for example, Germann et al.; Ikuta et al.) Appropriate substituents include alkyl or alkenyl groups having at least twelve carbon atoms, aryl groups containing at least two aromatic rings and at least 8 carbon atoms, or alkaryl groups comprising at least two aromatic rings and containing at least 9 carbon atoms. Suitable alkyl or alkenyl groups include stearyl, oleyl, or myristoyl. The aromatic rings in aryl or aralkyl groups may be linked, as in a biphenyl or trityl structure, fused, as in a naphthyl- or phenanthryl-containing group, or part of a multiring structure such as fluorescein. Substituted or unsubstituted trityl or pixyl groups are preferred, and 4,4'-dimethoxytrityl (DMT) is particularly preferred.

The phosphate linkage may be adjacent to the hydrophobic substituent, i.e. at the 3'carbon in ribofuranose numbering, as shown in formula I below (where PN represents a polynucleotide chain linked to the phosphate group via a 3'-terminal or 5'-terminal oxygen), or it may be at the 2' carbon, as shown in formula II. For ease of preparation, as described below, the regioisomer shown in formula I is preferred.

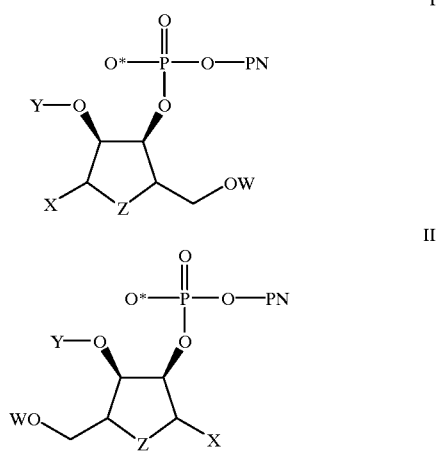

The ring may be further substituted as shown by the substituent X in FIG. 1. This group is preferably hydrogen, a lower alkoxy group, such as methoxy, or a nitrogen-linked heteroaryl group. In particular, when the cyclic moiety is derived from a ribofuranoside, the heteroaryl group is a purine or pyrimidine base.

Any diastereomer of the cyclic diol monophosphate may be used as long as the hydroxyl and phosphate groups are in a cis relationship. The relative stereochemistry of X and the hydrophobic substituent may vary; preferably, however, the linkage to the hydrophobic substituent is in a trans relationship to the hydroxyl and phosphate groups.

For ease of preparation, the hydrophobic group is preferably attached via a primary ether linkage to the deoxyribose ring (i.e., a —CH$_2$O— group), as shown, although for functional considerations, the hydrophobic group may be linked to the ring via any stable linkage, e.g. a secondary ether or alkyl linkage.

Figure 2A:
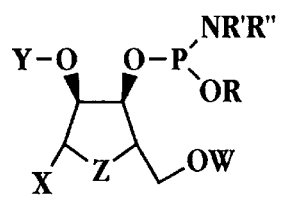
FIGS. 2A–2B show reactive phosphoramidite precursors to hydrophobic diol phosphate esters such as shown in FIGS. 1A–1B.
Figure 2B:
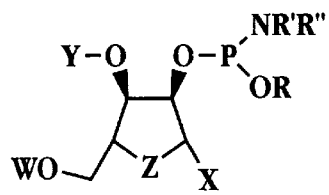

A polynucleotide product containing a terminal cyclic moiety, of which two examples are shown in FIGS. 1A–1B, is prepared by reacting a terminal 3'-hydroxyl or 5'-hydroxyl of a protected polynucleotide chain with a reactive cyclic phosphorylated monomer, such as an activated phosphotriester or, preferably, a cyclic phosphoramidite, as shown in FIGS. 2A–2B. The phosphoramidite group, when activated under mild acidic conditions, is effective to react with a free hydroxyl group on the polynucleotide to form a phosphite linkage, which is then oxidized to a phosphate linkage. The remaining substituents on the ring, and the preferred stereochemistry, are as described above. FIG. 2B represents a cyclic phosphoramidite used to form polynucleotide adducts represented by formula II above, where the positions of the hydrophobic substituent and (protected) hydroxyl group are reversed with respect to formula I.

The hydroxyl group of the reactive phosphoramidite compound of FIG. 2 is protected with a 2'- or 3'-hydroxyl protecting group, shown as Y, to prevent intramolecular reaction, or intermolecular reaction with the phosphoramidite group of another molecule. The protecting group is one that is stable to reagents and conditions used in oligonucleotide synthesis; in particular, it is not removed by weakly acidic or basic condensation or capping catalysts, such as tetrazole or N-methylimidazole, oxidation reagents, acidic detritylation reagents, or reagents, typically aqueous ammonia, used to cleave the polynucleotide from a solid reaction support.

Preferably, the group is one that is removable under non-acidic conditions. Selectively removable hydroxyl protecting groups have been extensively studied and are described, for example, in Kocienski, Ch. 2. Preferred groups for the present application include silyl ethers, which are removable by treatment with fluoride under neutral or near-neutral conditions. Groups removable by hydrogenolysis, such as benzyl ethers, or by photolysis, such as o-nitrobenzyl ethers, may also be used. Of these protecting groups, silyl ethers are preferred. Suitable silyl ethers include tert-butyl diphenyl, triisopropyl, and tert-butyl dimethyl. Tert-butyl dimethyl silyl (TBDMS) ethers, which have good base stability but are readily removed by fluoride ion, are particularly preferred.

R represents a phosphate protecting group removable by treatment with a nucleophile or base. Such protecting groups known in the art include methyl and halophenyl, such as 2-chlorophenyl and 2,5-dichlorophenyl. Preferred protecting groups are those removable by base-catalyzed beta-elimination, as described by Koester et al. Such a group is preferably beta-substituted lower alkyl, and particularly beta-substituted ethyl, where the beta-substituent is an electron withdrawing group. Preferred substituents include halogen, cyano, nitro, trihalomethyl, phenyl, thiophenyl, phenylsulfoxy and phenylsulfonyl, where the phenyl groups may be substituted at the ortho or para positions with halogen, cyano, or nitro. Most preferable is beta-cyanoethyl.

The amino group bound to the phosphorus atom, which will act as a leaving group in attachment of the compound to a polynucleotide, is substituted with two groups R' and R" which are independently alkyl, aryl, aralkyl, or $C_5$ to $C_{10}$ cycloalkyl, or the two groups taken together with the nitrogen atom may form a saturated 5- or 6-membered ring whose ring atoms are selected from carbon, nitrogen, oxygen, and sulfur.

III. Preparation of Polynucleotide with Attached Hydrophobic Moiety

A. Polynucleotide Component

The polynucleotide component of the present composition and method may be prepared according to synthetic methods well known in the art, which are described briefly here.

1. Attachment to Solid Support

Stepwise synthesis of polynucleotides is almost universally carried out with the growing nucleotide chain attached to a solid reaction support. Common supports include controlled pore glass (CPG), silica gel, and polystyrene. The reaction support is typically amino-derivatized, using standard procedures, e.g. Wallace, pp. 638–639, and Atkinson, pp. 45–49. Polystyrene supports are treated, for example, with hydroxymethylphthalimide, catalyzed by methylsulfonic acid, to form phthalimidomethyl polystyrene. This material is treated with hydrazine to remove the phthalimide protecting group, giving aminomethylated polystyrene. Controlled pore glass is typically functionalized by treatment with aminopropylsilane, as described in Atkinson.

The amine-derivatized support is then linked to a 5'-blocked or 3'-blocked protected nucleoside, as defined below, which forms the first nucleoside of the polynucleotide to be synthesized. Preferably, the first blocked, protected nucleoside is linked to the support by way of a base-labile linkage, such as a succinate group (see e.g. Atkinson; Caruthers, 1984). The linkage is formed by reacting, for example, an activated 3'-blocked protected nucleoside-5'-O-succinate with an amino-derivatized support. Such a linkage is shown at the first structure (1) in FIG. 5. Unreacted amine groups of the support are then rendered inactive by acylation with a monocarboxylic acid, or preferably, with acetic anhydride.

2. Nucleoside Monomers

The nucleoside monomers used in stepwise synthesis of the polynucleotide are blocked at the 3'or 5'functional group, which is generally a hydroxyl group. The blocking group is preferably acid-labile, in that it can be removed so as to expose the reactive group upon mild acid treatment. Preferably, the blocking group is a trityl ether, and most preferably a 4,4'-dimethoxytrityl (DMT) ether. Synthesis of such blocked nucleoside intermediates is well know in the art, e.g. Caruthers et al., 1984, 1985. The trityl blocking groups may be removed by exposure to 3% dichloroacetic acid for about 1–4 minutes at room temperature.

The exocyclic amines of nucleoside monomers are protected by acylation (see, e.g., Jones, pp. 23–34) to prevent them from participating in the synthetic reactions, with the exception of thymidine and uridine, which do not require amine protection. Preferably, the exocyclic amine protection groups are sufficiently base-labile so that the polynucleotide chains can be deprotected and cleaved from the solid reaction support in the same step. Preferred amine protecting groups for this purpose, such as described in Molko et al., include acid chlorides, such as methoxyacetyl chloride, benzoyl chloride, isobutyryl chloride, or phenoxyacetyl chloride, and the corresponding acid anhydrides.

The internucleoside phosphate of phosphoramidite intermediates is protected by a phosphate protecting group removable by treatment with a nucleophilic or basic reagent, preferably a group which may be removed by beta-elimination, as described above with reference to the compounds of FIGS. 2A–2B. Most preferable is beta-cyanoethyl.

Deprotection and cleavage from the support, after synthesis is complete, can be achieved by treating with concentrated (29%) ammonia at 55° C. for 1–16 hours, depending on the particular protecting groups used.

3. Monomer Coupling Steps

Detailed procedures for the phosphoramidite and hydrogen phosphonate methods of polynucleotide synthesis are described in the following references, which are incorporated by reference: Caruthers et al. 1984, 1985; Koester et al.; Matteucci et al.; Jones; Atkinson et al.; Garegg et al.; Froehler; Froehler et al.; Usman et al.; and Andrus et al. Phosphorothioate analogs of polynucleotides can be synthesized by following the thionization steps taught by Froehler for H-phosphonate chemistry, or by Stec et al. for phosphoramidite chemistry.

Preparation of a recently developed class of polynucleotide analog, N3'→P5' phosphoramidates, is described in McCurdy et al. Each coupling in the synthesis, which proceeds in the 5' to 3' direction, employs a phosphoramidite amine exchange reaction, using 1H-tetrazole-activated 5'-phosphoramidite-3'-(trityl)amino-protected nucleoside monomers, followed by oxidation, as described in Example 1A.

The above internucleotide linkages can be used with DNA nucleoside subunits, or with 2'-alkoxy RNA subunits. DNA/RNA chimeras may also be prepared by using a combination of the two.

Synthesis of the desired polynucleotide chain proceeds by performing repeated cycles of deblocking (i.e. removal of the 3'- or 5'- protecting group), monomer addition, oxidation, and capping. "Capping" refers to reaction of unreacted 5'-hydroxyls, in a 3' to 5' synthesis, or unreacted 3'-hydroxyls or amines in a 5' to 3' synthesis, with a capping agent after each condensation step. This renders such chains incapable of participating in subsequent condensation steps and thus forming incorrect-sequence oligomers. Commonly used capping agents include phosphite monoesters and carboxylic anhydrides. Such capped chains do not react with the cyclic phosphoramidites of FIGS. 2A–2B in the final step of the synthesis and thus do not contain the hydrophobic substituent W when the synthesis is complete.

The purification method described herein is suitable for any of the above-described polynucleotides or polynucleotide analogs. In particular, certain polynucleotide analogs, such as phosphodiesters and phosphorothioates, are susceptible to depurination in acid. The deprotected internucleotide linkages in a N3'→P5' phosphoramidate are likewise somewhat unstable to the acidic conditions typically used for removal of trityl groups after chromatographic purification by RP-HPLC. The present invention is particularly useful in such instances, in that the hydrophobic group used in purification of the polynucleotide, such as trityl or DMT, can be removed under non-acidic conditions, as described below.

B. Preparation of the Hydrophobic Cyclic Moiety

In a preferred embodiment, the cyclic moiety is derived from a ribofuranoside, having the preferred relative stereochemistry shown in FIGS. 2A–2B. One such moiety is the commercially available (Glen Research) RNA monomer, 5'-O-DMT-2'-O-TBDMS-uridine-3'-(2-cyanoethyl)-N,N-diisopropylaminophosphoramidite. Other ribosides (or ribonucleosides), where X in FIGS. 2A–B is a purine or pyrimidine base, are also readily available.

Figure 3A:
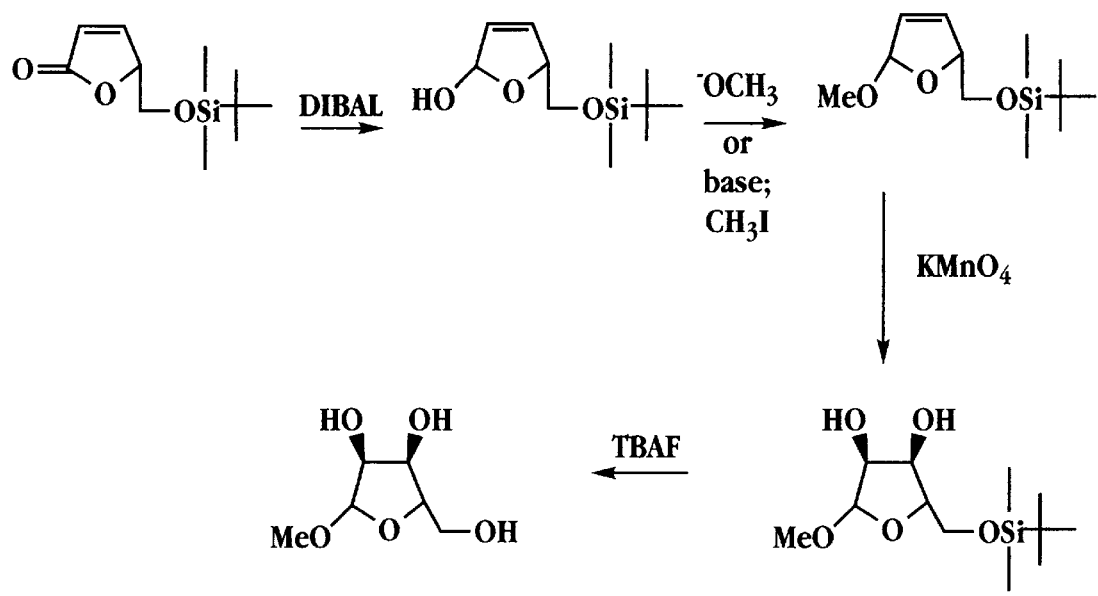
FIGS. 3A–3B illustrate routes of preparing diol and triol precursors to the compounds of FIGS. 2A–2B.

Alkoxy-substituted ribofuranoses, i.e. where X is lower alkoxy, may be obtained commercially or prepared by standard synthetic methods. For example, a protected 5-(hydroxymethyl)-2(5H)furanone (FIG. 3A), derived from D-mannitol (Jeong et al.) is converted to the 2-alcohol by selective reduction with DIBAL, and the alcohol is then converted to a lower alkyl ether, as shown. Oxidation of the 3,4-double bond with $KMnO_4$ then gives the desired cis-diol. Substitution of a cyclopentenone for the furanone in this process gives the corresponding diol where Z is —$CH_2$—.

Figure 3B:
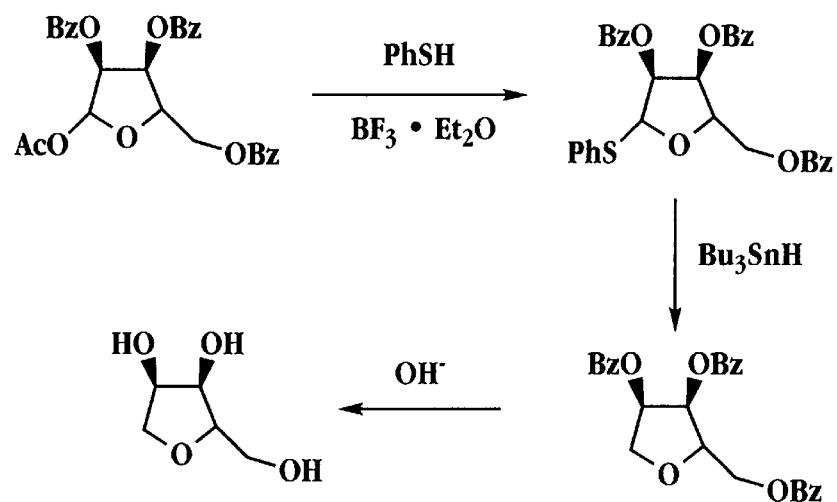

1-Deoxy ribofuranoses, where X=hydrogen, may be prepared by similar reaction of hydroxymethyl-substituted cyclopentenes or dihydrofurans; see, for example, procedures described in Leeson et al. The preparation of such compounds from commercially available 1-O-acetyl-2,3,5-tri-O-benzoyl-D-ribofuranose is also described in Beigelman et al. (FIG. 3B). The preferred route involves $BF_3$ etherate catalyzed thiophenylation at the 1-position and subsequent reduction with tributyltin hydride; deprotection gives the cis-diol.

Any of the above described diols or triols may be selectively substituted to give a structure as shown in FIG. 2A or 2B. According to one synthetic scheme, the 2'- and 3'-hydroxyls are incorporated into a ketal, such as an acetonide, and the free 5'-hydroxyl is converted to the desired hydrophobic group, such as a trityl ether. The ketal is removed, and the cis-diol compound is then reacted with one equivalent of a silyl chloride. This approach typically produces a mixture of the two regioisomers, which may then be separated by standard chromatographic methods, as reported in Beigelman. Alternatively, methods reported by Hakimelahi et al. may be used to obtain good selectivity of the 3'-silylated isomer, the precursor to FIG. 2B. After purification, chloro-N,N-diisopropylamino methoxy phosphine is reacted with the remaining hydroxyl group.

This route may also be used to prepare compounds where the hydrophobic group is attached via a secondary, rather than a primary, ether. Since the 2'- and 3'-secondary hydroxyl groups are both blocked, the increased selectivity provided by a primary hydroxyl group is not required. However, a primary hydroxyl is nonetheless preferred since less stringent conditions are required for its reaction with a bulky hydrophobic group.

Figure 4:
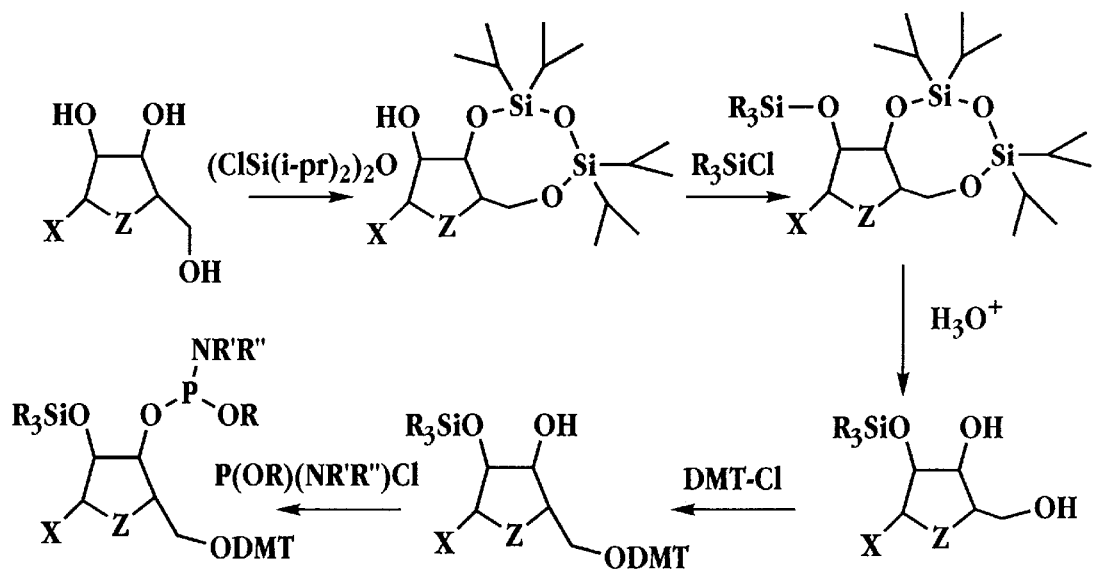
FIG. 4 shows a method of preparing a compound as shown in FIG. 2A.

The strategy shown in FIG. 4 gives the 2'-silylated isomer. As shown, the 3' and 5' hydroxyls are reacted with 1,3-dichloro-1,1,3,3-tetraisopropyldisiloxane (Markiewicz) to form a cyclic disiloxane. The free 2' hydroxyl is then reacted with a silyl chloride, such as triisopropyl or t-butyldiphenyl silyl chloride, to give the protected hydroxyl. These reagents are preferred for this synthetic route because the cyclic disiloxane may then be removed selectively under conditions, such as aqueous acid at room temperature, which do not affect the more robust triisopropyl or t-butyldiphenyl silyl ethers (Kocienski). A hydrophobic group is attached at the primary 5' hydroxyl, which reacts preferentially, by reaction with, e.g., trityl chloride. The 3' secondary hydroxyl is then reacted with an activated phosphine, such as chloro-N,N-diisopropylamino methoxy phosphine, to give the desired phosphoramidite.

C. Attachment of the Hydrophobic Cyclic Moiety to the Polynucleotide

Because the hydroxyl-protected cyclic moiety A or B, as shown in FIGS. 2A–2B, includes a phosphoramidite group, it can generally be conveniently attached to a polynucleotide chain using the same reagents and methods employed in the synthesis of the polynucleotide. Thus, the terminal 3' or 5' hydroxyl group of the polynucleotide chain is deprotected, e.g. by acid-catalyzed removal of a trityl protecting group, the phosphoramidite is activated by the addition of tetrazole, and coupling takes place, in an air- and moisture-free atmosphere, to form a phosphite triester product. The phosphite triester is then oxidized to form the corresponding hydroxyl-protected 3'- or 5'-polynucleotide diol phosphate triester.

Figure 5:
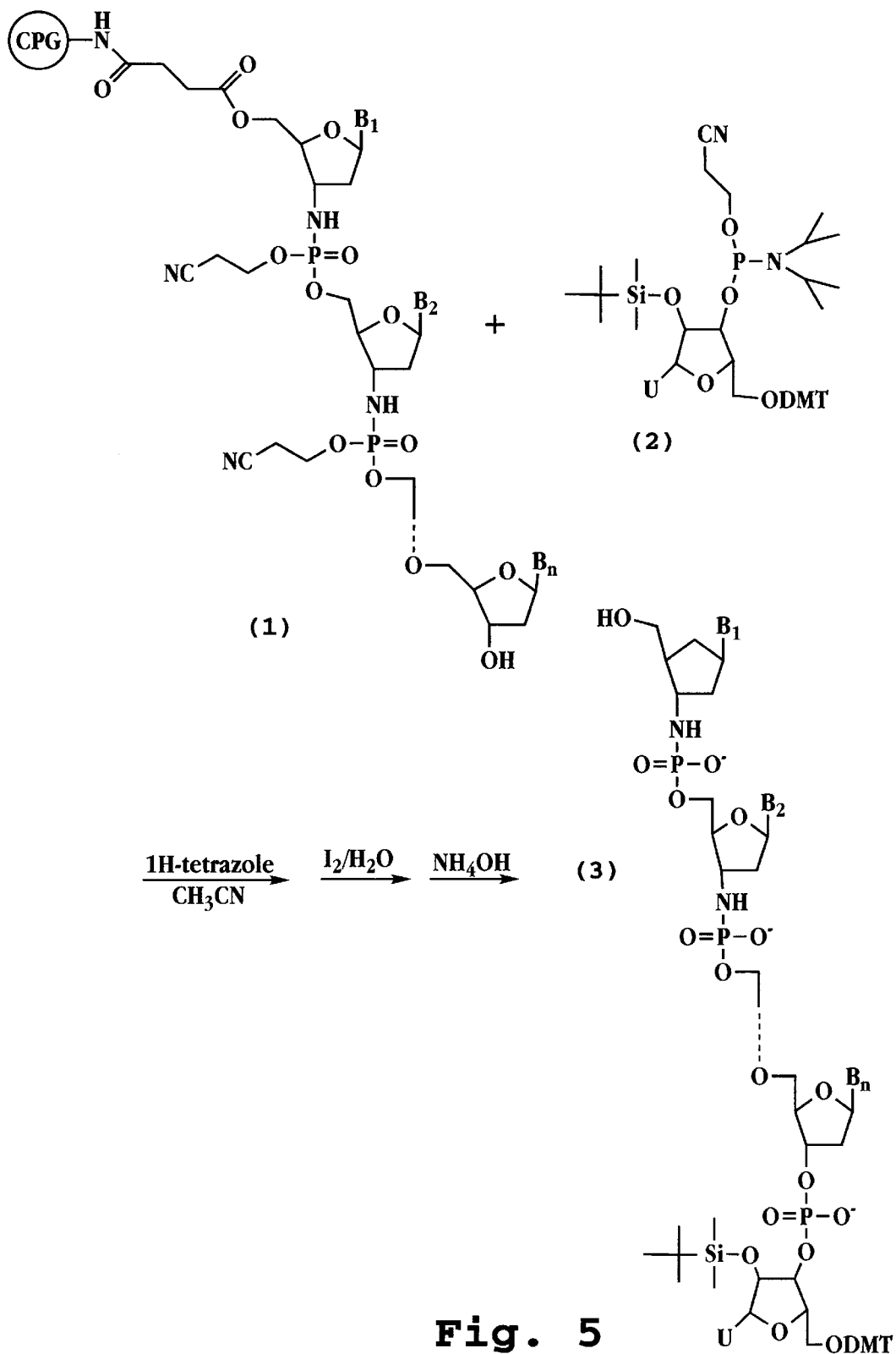
FIG. 5 illustrates the synthesis of a N3'→P5' phosphoramidite oligonucleotide product having a hydrophobic diol phosphate ester at its 3'-terminus.

For preparation of N3'→P5' phosphoramidate polynucleotides, as described in Example 1, a 3'-hydroxyl-, rather than a 3'-amino-, nucleoside is used in the final coupling step, prior to addition of the terminal cyclic moiety, as shown in structure (1) in FIG. 5. Because the polynucleotide chain is synthesized in the 5' to 3' direction, the resulting phosphate diester linkage between the polynucleotide chain and the terminal moiety, shown in structure (3), is a 3'-3' phosphodiester linkage.

IV. Purification Method

After the completion of synthesis and attachment of the hydrophobic diol phosphate ester, as described above, the polynucleotide product is cleaved from the reaction support. Cleavage may be accomplished by treatment with concentrated ammonium hydroxide:ethanol (3:1) for 8–16 hours at 55° C. This treatment also deprotects the exocyclic amines of the nucleotides and the internucleotide phosphate linkages. The resulting cleavage mixture includes the desired-sequence polynucleotide product with the attached hydrophobic diol phosphate ester, e.g. structure (3) in FIG. 5, as well as undesired components such as capped failure sequences.

The cleavage mixture is optionally concentrated and then diluted with a concentrated alkylammonium salt solution, such as 2M triethylammonium acetate or triethylammonium bicarbonate, to establish a lipophilic counterion (see Example 1).

The mixture is then applied to a hydrophobic solid phase adsorbent that preferentially adsorbs the derivatized polynucleotide containing the attached hydrophobic moiety. The preferential adsorption is accomplished by selection of a hydrophobic substituent and solid phase adsorbent which have a strong mutual attraction relative to the rest of the polynucleotide. A preferred solid phase adsorbent is highly crosslinked polystyrene, such as a PLRP-S reverse phase HPLC column (Polymer Labs), as demonstrated in Example 1. However, other hydrophobic supports, including commercially available purification cartridges, may also be used. The preferred hydrophobic substituents of the present invention, which incorporate two or more phenyl rings, are preferentially adsorbed onto such supports on the basis of hydrophobicity. Long chain alkyl or alkenyl groups have also been found effective as hydrophobic substituents.

Components which do not contain the attached diol phosphate ester and hydrophobic substituent may then be eluted, using conditions under which the derivatized polynucleotide product remains bound to the support. Such components include capped polynucleotide failure sequences, as described above. Typically, a solvent gradient is used for elution, as described in the Example.

Figure 6:
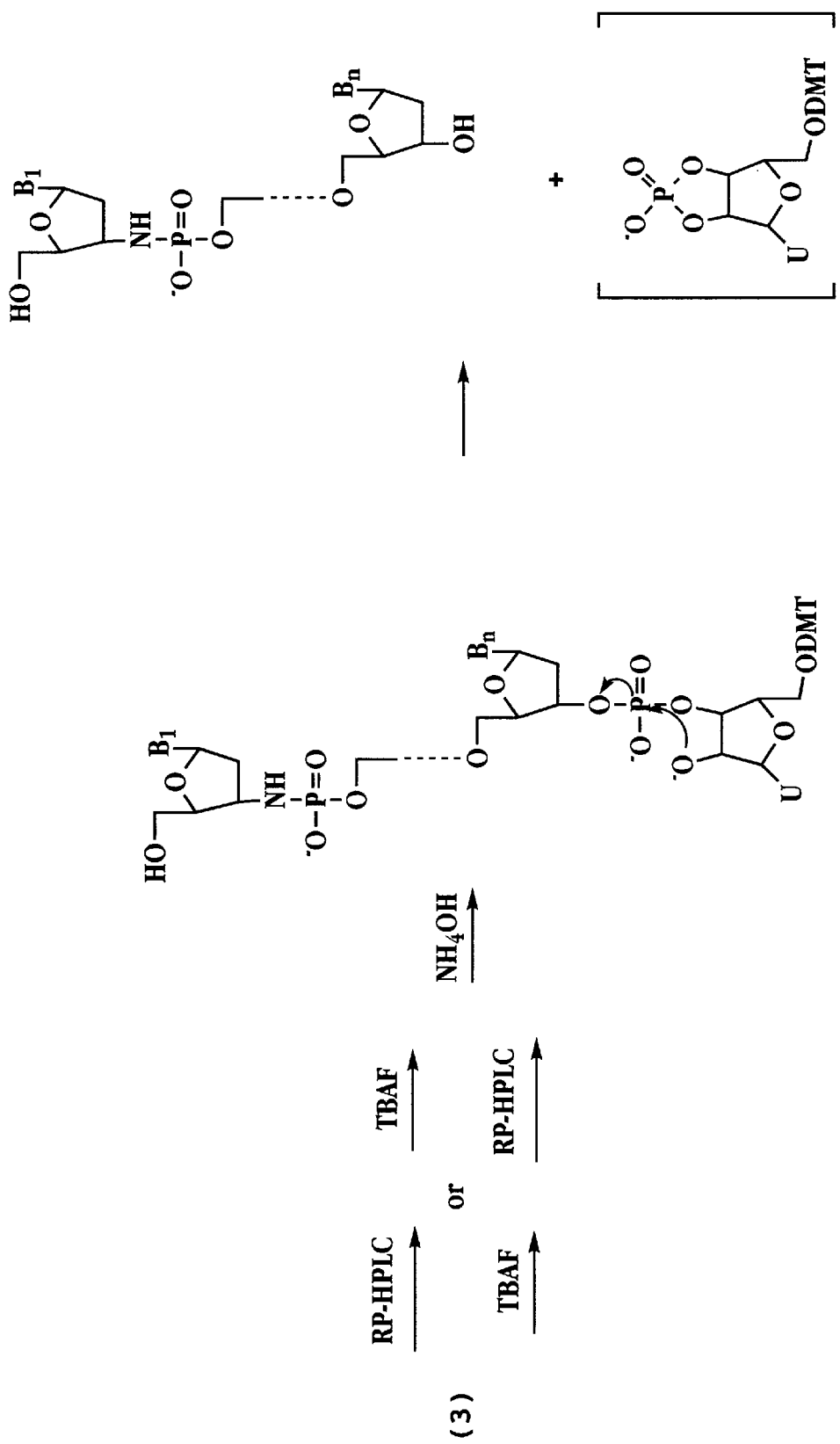
FIG. 6 illustrates the removal of the hydrophobic moiety from the oligonucleotide of FIG. 5, subsequent to purification by HPLC.

The desired-sequence, derivatized polynucleotide, e.g. structure (3), containing the attached diol phosphate ester, is then eluted from the support. The isolated derivatized polynucleotide is then treated to remove the hydroxyl protecting group Y, generating a free hydroxyl group, as shown in FIG. 6. Preferably, the protecting group is removed under non-acidic conditions, especially for acid-sensitive polynucleotide analogs such as N3'→P5' phosphoramidates and purine-rich phosphodiesters and phosphorothioates. In a particularly preferred embodiment, where Y is a silyl protecting group, the treatment comprises treating the polynucleotide adduct with a source of fluoride ion. Suitable reagents are aqueous NaF or tetrabutylammonium fluoride.

This deprotection step may also be performed before the adsorbing step, i.e. before chromatographic purification, by treating the cleavage mixture with fluoride ion, and then performing RP-HPLC as described above. In either case, a purified polynucleotide product, containing a terminal moiety with a free hydroxyl group, as shown in FIG. 6, is obtained.

Removal of the cyclic moiety, along with the hydrophobic substituent, may then be accomplished by treatment with base. This effects a base-catalyzed cleavage of the phosphate linkage between the terminal moiety and the polynucleotide, as shown in FIG. 6, giving the final, underivatized polynucleotide product. The cleaved monomeric phosphate, which typically degrades to a mixture of 2'- and 3'-phosphate monoesters, is easily removed from the polynucleotide product, as described in the Examples below.

Because acid treatment is avoided, this method of removal of the hydrophobic (e.g. trityl or DMT) group is especially advantageous for acid-sensitive polynucleotide analogs, as noted above.

Figure 7:
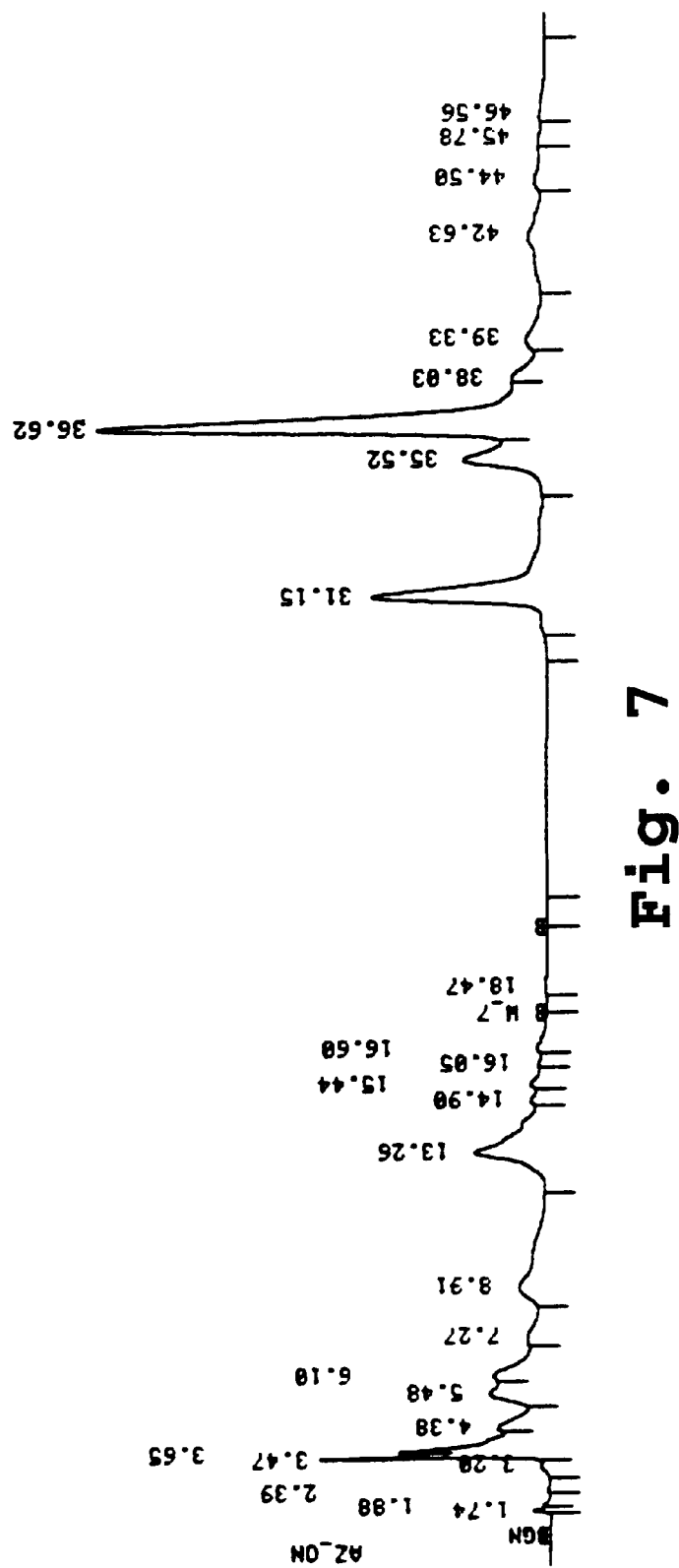
FIG. 7 shows an RP-HPLC trace of the reaction mixture obtained from the preparation of an N3→P5' phosphoramidate oligonucleotide having the sequence 5'-CCCTCCTCCGGAGCC-2'-O-TBDMS-U-$_{ODMT}$-3', performed on a 0.9×25 cm Polymer Labs PLRP-S column, as described in Example 1.

FIG. 7 shows a representative RP-HPLC trace from the purification of a N3'→P5' phosphoramidate oligonucleotide having the sequence 5'-CCCTCCTCCGGAGCC-U-(2'-O-TBDMS)$_{ODMT}$-3', as described in Example 1, prior to removal of the attached hydrophobic moiety. Two product peaks are seen due to premature removal of some of the 2'-protecting group, TBDMS, by the ammonia treatment. The product peaks combine to 42.9% of the total area.

FIG. 8 shows an IEC trace of the oligonucleotide after RP-HPLC purification (FIG. 7), removal of the attached cyclic phosphate ester with its hydrophobic substituent, and desalting. The purity was determined to be approximately 92%.

This RP-HPLC purification method was successfully scaled-up to 200 μmol for the sequence given above, giving identical results to those shown for a 1 μmol scale, as described in Example 1, below. The hydrophobic purification handle can be coupled to the terminal hydroxyl group of any oligonucleotide or analog and used to facilitate RP-HPLC purification, as long as the oligonucleotide analog is stable to the basic fluoride deprotection conditions.

The following example illustrates but is not intended in any way to limit the invention. This example illustrates the method as applied to the purification of a N3'→P5' phosphoramidate oligonucleotide; similar results have been obtained using a phosphodiester—N3'→P5' phosphoramidate chimera and a phosphorothioate—N3'→P5' phosphoramidate chimera.

EXAMPLE 1

A. Preparation of a N3'→P5' phosphoramidate oligonucleotide

A 1 μmol N3'→P5' phosphoramidate oligodeoxynucleotide (ODN) containing a terminal 3'-O-DMT group was synthesized on a Perkin Elmer/Applied Biosystems 392 synthesizer using the protocol described in *Tetrahedron Lett.*, Vol. 38, No. 2, pp. 207–210, 1997, except that 1.5% hydrogen peroxide/3.50% water/20% pyridine/THF was used in place of the iodine reagent and a 1:1 mixture of isobutyric anhydride/2,6-lutidine/THF (1/1/8) and NMI/THF (Perkin Elmer/ABI) was used for capping (2 minutes) after the final oxidation step. The synthesis was performed in the TRITYL-ON mode with MANUAL cleavage. The sequence was 5'-CCCTCCTCCGGAGCC$_{O-DMT}$-3'.

B. Attachment of hydrophobic handle (protected, hydrophobically substituted diol phosphoramidite).

A 0.1 M solution of 5'-O-DMT-2'-O-TBDMS-uridine-3'-(N,N'-diisopropylamino)-2-cyanoethylphosphoramidite (Glen Research) in acetonitrile was coupled to the 3'-terminal OH group of the ODN, after removal of the 5'-trityl group, using the standard RNA protocol for the 392 instrument (Perkin Elmer/ABI), except that hydrogen peroxide was used for oxidation (2 minutes) and the 1:1 mixture of the isobutyric anhydride formulation and NMI formulation, described above, was used for capping (2 minutes). The synthesis was performed in the TRITYL-ON mode with MANUAL cleavage.

C. Cleavage from support. The CPG-bound amidate ODN was dried in vacuo for 30 minutes, transferred to a 4 mL screw cap vial, and cleaved and deprotected with 0.75 mL of concentrated aqueous ammonia and 0.25 mL of absolute ethanol at 58° C. for 8–16 hours. After cooling the mixture, the CPG was filtered and washed with 3×0.5 mL of 3:1 concentrated aqueous ammonia:ethanol.

D. RP-HPLC Purification

The above solution was concentrated to ca. 0.5 mL, filtered, washed with 2×0.4 mL of water, and 0.15 mL of 2 M triethylammonium acetate and 0.03 mL of acetonitrile were added. The crude ODN cleavage mixture was analyzed by ion exchange chromatography (IEC). IEC was performed on a Dionex PA-100 column (4×250 mm) using a gradient of 0:100 A:B to 20:80 A:B over 10 minutes, then 20:80 A:B to 50:50 A:B over 30 minutes, at 1 mL/min, and detection at 260 nm. Buffer A=0.01 M NaOH/0.01 M NaCl/H$_2$O; Buffer B=0.01 M NaOH/1.5 M NaCl/H$_2$O. Full length purity=40.1%.

The cleavage mixture was purified by reverse phase (RP) HPLC (FIG. 7). For HPLC, a PLRP-S column was used (Polymer Labs, 0.9 cm×25 cm) with the following solvent gradient: 5:95 to 40:60 A:B over 40 minutes, then hold at 40:60 A:B for 10 minutes before re-equilibration, where A=acetonitrile and B=0.1 M triethylammonium bicarbonate/2% acetonitrile/pH 8. The flow rate was 2 mL/min and detection was at 296 nm.

The peaks at 31.15 min and 36.62 min are both product peaks and combine to 42.9%. Two "product" peaks are seen by RP-HPLC, due to premature removal of some of the TBDMS group by the ammonia treatment. Both product peaks were collected (as shown in FIG. 7) and concentrated to dryness in the savant.

E. Removal of hydrophobic handle.
Method 1. The dry RP-HPLC purified N3'→P5' phosphoramidate ODN, 5'-CCCTCCTCCGGAGCC-U-(2'-O-TBDMS)$_{ODMT}$-3', was treated with 0.2 mL 1 M tetrabutylammonium fluoride in THF and 0.2 mL of 1 M aqueous NaOH at room temperature for 4 hours.

When the cleavage of the uracil group was complete (IEC), the sample was diluted with 1 mL of sterile water and desalted on a PD-10 column (Pharmacia) to remove the uracil by-products. The counter ion of the phosphoramidate ODN was fully converted to sodium by several precipitations from 1 M aqueous NaCl with 2.5 volumes of ethanol.
Method 2.

The uracil purification handle was removed by treatment with 0.2 mL of 1 M aqueous NaF and 0.2 mL of concentrated aqueous ammonia at 58° C. for 12 hours. After concentration of the solution to ca. 0.2 mL, the ODN was precipitated with 0.6 mL of ethanol, redissolved in 0.5 mL of sterile water, and desalted on a NAP-5 column (Pharmacia). The purified, desalted pnODN was then lyophilized. The concentration of ODN was determined at 260 nm (17.7 OD; 14.7% overall yield) and the purity (91.9%) was determined by IEC (FIG. 8), performed as described above.

While the invention has been described with reference to specific methods and embodiments, it will be appreciated that various modifications may be made without departing from the invention.

It is claimed:

1. A method of purifying a polynucleotide product, the method comprising the steps of:
   (a) forming a 3'- or 5'-polynucleotide cis-diol phosphate diester, in which a cis-diol phosphate diester moiety is attached at the 3'- or 5'-terminus of a polynucleotide chain, as represented by formula I or II below:

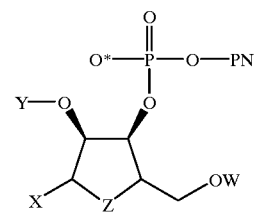

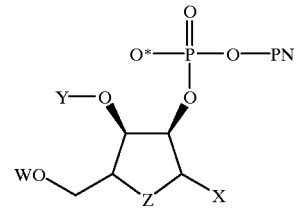

where:
PN consists of a polynucleotide chain,
W is a hydrophobic group;
X is selected from the group consisting of hydrogen, lower alkoxy, and nitrogen-linked heteroaryl;
Y is hydrogen or a 2'- or 3'-hydroxyl protecting group; and
Z is oxygen or —CH$_2$—;
wherein the absolute configuration of the cis-diol is selected from the configuration depicted, the opposite configuration to that depicted, and a mixture of absolute configurations;
   (b) selectively adsorbing the polynucleotide diol phosphate diester onto a hydrophobic solid-phase support;
   (c) eluting the polynucleotide diol phosphate diester from the support to yield a purified polynucleotide product;
   where Y is a 2'- or 3'-hydroxyl protecting group, removing said protecting group from the polynucleotide diol phosphate diester; and
   (d) after said eluting, treating the polynucleotide diol phosphate diester with base, thereby cleaving the diol phosphate moiety from said polynucleotide.

2. The method of claim 1, wherein X is a purine or pyrimidine base.

3. The method of claim 1, wherein said removing is done before adsorbing step (b).

4. The method of claim 1, wherein said removing is done after eluting step (c).

5. The method of claim 1, wherein said polynucleotide chain comprises at least one N3'→P5' phosphoramidate intersubunit linkage.

6. The method of claim 1, wherein said polynucleotide chain comprises at least one phosphodiester or phosphorothioate intersubunit linkage.

7. The method of claim 1, wherein said polynucleotide chain comprises at least one 2'-alkoxy RNA nucleotide subunit.

8. The method of claim 1, wherein said polynucleotide diol phosphate diester is represented by formula I.

9. The method of claim 1, wherein Z is oxygen.

10. The method of claim 1, wherein said hydrophobic group is selected from the group consisting of an alkyl group having at least twelve carbon atoms, an aryl group containing at least two aromatic rings and at least 8 carbon atoms, and an aralkyl group comprising at least two aromatic rings and containing at least 9 carbon atoms.

11. The method of claim 10, wherein the hydrophobic group is an unsubstituted or substituted trityl or pixyl group.

12. The method of claim 11, wherein the hydrophobic group is 4,4'-dimethoxytrityl.

13. The method of claim 1, wherein Y is $SiR^2R—R^3$, where $R^1$, $R^2$ and $R^3$ taken separately are selected from the group consisting of lower alkyl, lower haloalkyl, and aryl.

14. The method of claim 13, wherein $R^1=R^2=$methyl and $R^3=$tert-butyl.

15. The method of claim 13, wherein said removing of the Y group is accomplished using fluoride ion.

16. The method of claim 1, wherein said forming of said 3'- or 5'-polynucleotide cis-diol phosphate diester further comprises (i) reacting a polynucleotide having a free 3'- or 5'-hydroxyl group with a protected cis-diol phosphoramidite represented by formula A or B below, wherein the absolute configuration of the cis-diol is selected from the configuration depicted, the opposite configuration to that depicted, and a mixture of absolute configurations:

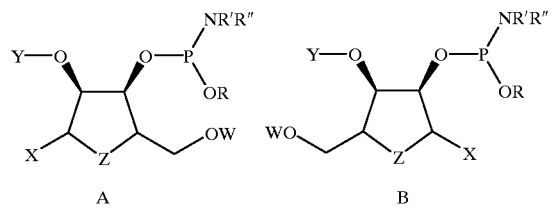

where:
W is a hydrophobic group;
X is selected from the group consisting of hydrogen, lower alkoxy, and a nitrogen-linked heteroaryl;
Y is a 2'- or 3'-hydroxyl protecting group;
Z is oxygen or —$CH_2$—;
R is a phosphate protecting group; and
R' and R" are separately selected from the group consisting of alkyl, aryl, aralkyl, and $C_5$ to $C_{10}$ cycloalkyl, or R' and R" taken together with the nitrogen atom to which they are attached form a saturated 5- or 6-member ring whose ring atoms are selected from the group consisting of carbon, nitrogen, oxygen, and sulfur;
thereby forming a protected 3'- or 5'-polynucleotide cis-diol phosphite triester;
(ii) oxidizing said phosphite triester and removing said phosphate protecting group R, to form a phosphate diester; and, where Y of formula I or II is hydrogen,
(iii) removing said 2'- or 3'-hydroxyl protecting group.

17. The method of claim 16, wherein said protected diol phosphoramidite is represented by formula A.

18. The method of claim 16, wherein R is selected from the group consisting of methyl, lower alkyl beta-substituted with at least one electron-withdrawing group, and halo-substituted aryl.

19. The method of claim 18, wherein R is methyl or β-cyanoethyl.

20. The method of claim 16, where R'=R"=isopropyl.

* * * * *